US006689131B2

(12) United States Patent
McClurken

(10) Patent No.: US 6,689,131 B2
(45) Date of Patent: Feb. 10, 2004

(54) ELECTROSURGICAL DEVICE HAVING A TISSUE REDUCTION SENSOR

(75) Inventor: Michael E. McClurken, Durham, NH (US)

(73) Assignee: TissueLink Medical, Inc., Dover, NH (US)

(*) Notice: Subject to any disclaimer, the term of this patent is extended or adjusted under 35 U.S.C. 154(b) by 0 days.

(21) Appl. No.: 09/802,288

(22) Filed: Mar. 8, 2001

(65) Prior Publication Data

US 2002/0128650 A1 Sep. 12, 2002

(51) Int. Cl.⁷ ............................................... A61B 18/18
(52) U.S. Cl. ........................... 606/48; 606/41; 606/49; 606/50; 606/51; 607/101; 607/104
(58) Field of Search .............................. 606/32, 39, 40, 606/41, 45, 48, 49, 50, 51, 52; 604/20, 114; 607/96, 101, 104, 105, 113

(56) References Cited

U.S. PATENT DOCUMENTS

| | | |
|---|---|---|
| 5,458,596 A | 10/1995 | Lax et al. |
| 5,514,130 A | 5/1996 | Baker |
| 5,569,242 A | 10/1996 | Lax et al. |
| 5,660,836 A | 8/1997 | Knowlton |
| 5,755,753 A | 5/1998 | Knowlton |
| 5,785,705 A | 7/1998 | Baker |
| 5,843,078 A | 12/1998 | Sharkey |
| 5,871,524 A | 2/1999 | Knowlton |
| 5,919,219 A | 7/1999 | Knowlton |
| 5,954,716 A | 9/1999 | Sharkey et al. |
| 6,033,398 A | 3/2000 | Farley et al. |
| 6,035,238 A | 3/2000 | Ingle et al. |
| 6,081,749 A | 6/2000 | Ingle et al. |
| 6,091,995 A | 7/2000 | Ingle et al. |
| 6,440,130 B1 * | 8/2002 | Mulier et al. ................. 606/49 |

FOREIGN PATENT DOCUMENTS

WO    WO 00/62727    10/2000

OTHER PUBLICATIONS

Finger, P. et al., "Heat Shrinkage of Extraocular Muscle Tendon", *Arch. Ophthalmol.*, vol. 105, No. 5, pp. 716–718 (May 1987).
Selecky, M. et al., "The Effects of Laser–Induced Collagen Shortening on the Biomechanical Properties of the Inferior Glenohumeral Ligament Complex", *Am. J. Sports Med.*, vol. 27, No. 2, pp. 168–172 (Mar./Apr. 1999).
Vangsness Jr., C. et al., "Collagen Shortening", *Clinical Orthopaedics and Related Research*, No. 337, pp. 267–271 (1997).
Wall, M. et al., "Thermal Modification of collagen", *Journal of Shoulder and Elbow Surgery*, vol. 8, No. 4, pp. 339–344 (Jul./Aug. 1999).

* cited by examiner

*Primary Examiner*—Rosiland Kearney Rollins
(74) *Attorney, Agent, or Firm*—Merchant & Gould P.C.; Mara E. Liepa, Esq.; Michael J. Gallagher, Esq.

(57) ABSTRACT

An electrosurgical device for use in surgical procedures is disclosed. The electrosurgical device comprises a main body having a proximal end and a distal end. A heat delivery modality is situated and arranged at the distal end of the main body. A sensor arrangement is also situated and arranged at the distal end of the main body. The heat delivery modality provides thermal energy to a tissue being treated while the sensor arrangement is configured to engage and detect a change in dimension of the tissue being treated. Accordingly, the electrosurgical device of the present disclosure allows a surgeon to precisely achieve the desired amount of dimensional change of the tissue being treated.

68 Claims, 10 Drawing Sheets

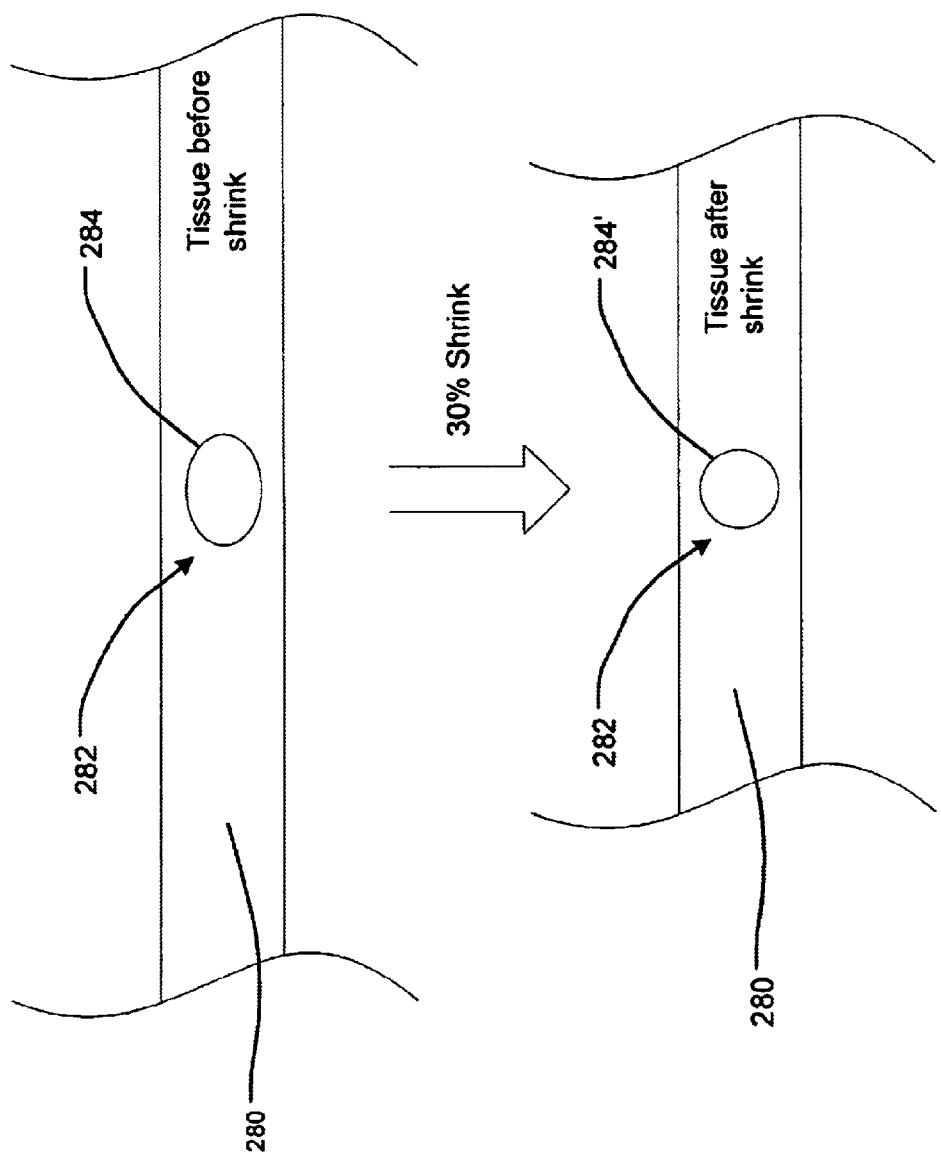

ELECTROSURGICAL DEVICE HAVING A TISSUE REDUCTION SENSOR

TECHNICAL FIELD

The present invention relates generally to electrosurgical devices for use in surgical procedures and, more particularly, to an electrosurgical device having a sensor for detecting a change in tissue dimension.

BACKGROUND

Electrosurgical devices use electrical energy, most commonly radiofrequency ("RF") energy, to cut tissue and/or cauterize blood vessels. During use, a voltage gradient is created at the tip of the device, thereby, inducing current flow and related thermal energy generation in the tissue. With appropriate levels of electrical energy, the thermal energy generated is sufficient to cut or shrink the tissue being treated, or cauterize blood vessels.

Existing electrosurgical devices can cause the temperature of the tissue being treated (e.g., the tissue treatment zone) to rise significantly higher than 100 degrees C., resulting in tissue desiccation, tissue sticking to the electrodes, tissue perforation, char formation and/or smoke generation. Peak tissue temperatures as a result of RF treatment can be as high as 350 degrees C., and such high temperatures may be transmitted to adjacent tissue via thermal diffusion. Undesirable results of such transmission to adjacent tissue include unintended thermal damage to the tissue. To reduce these undesirable results, electrosurgical devices have been developed that simultaneously introduce a fluid (e.g., an electrolytic solution with RF applications) to the tissue treatment zone, thereby, distributing the thermal energy at the tissue treatment zone, and providing cooling as well.

In many applications, it is often desirable to allow the surgeon or operator of the electrosurgical device to control the dimensional changes of the tissue being treated. Typically, this is accomplished by monitoring the temperature at or near the tissue treatment zone. With some electrosurgical devices, the surgeon or operator can manually control the thermal energy being introduced to the tissue treatment zone. Alternatively, other electrosurgical devices can be configured to operate with a feedback control system to automatically control the thermal energy introduced to the tissue being treated. In either case, shortcomings with existing electrosurgical devices limit their effectiveness in controlling the dimensional changes of the tissue being treated.

In particular, existing electrosurgical devices monitor the temperature at or near the tissue treatment zone using a temperature sensor, such as, a thermocouple, thermistor, phosphor-coated optical fibers, or some other temperature sensor. Various factors often influence the temperature read by the temperature sensor including the temperature of the tissue being treated as well as any fluid being simultaneously infused at the tissue treatment zone. Furthermore, the temperature being read by the temperature sensor varies as the surgeon or operator moves the electrosurgical device into or out of the tissue treatment zone. As a result of these and other factors, it is often difficult to precisely achieve the desired dimensional change (e.g., the amount of shrinkage) of the tissue being treated.

Improvements in electrosurgical devices used in surgical procedures are, therefore, sought.

SUMMARY

In general terms, the present disclosure relates to an electrosurgical device for use in surgical procedures. More particularly, the present disclosure relates to an electrosurgical device having a sensor for detecting a change in tissue dimension, such as, tissue expansion or contraction. In one aspect, the electrosurgical device comprises a main body having a proximal end and a distal end. A heat delivery modality is situated and arranged at the distal end of the main body. A sensor arrangement is also situated and arranged at the distal end of the main body. The heat delivery modality provides thermal energy to a tissue being treated while the sensor arrangement is configured to engage and detect shrinkage of the tissue being treated. In one particular aspect, the heat delivery modality can be configured to provide a continuous flow of electrically conductive fluid to the tissue being treated while thermal energy is introduced.

Further in this aspect, the sensor arrangement can comprise at least one contact sensor situated and arranged at the distal end of the main body. In this aspect, the at least one contact sensor is constructed and arranged to engage and detect the shrinkage of the tissue being treated. Alternatively, the sensor arrangement can comprise first and second clamping members that are situated astride the main body. In this aspect, the first clamping member can include a first end pivotably connected at the main body and a second end opposite the first end. Similarly, the second clamping member can include a first end pivotably connected at the main body and a second end opposite the first end. Each of the second ends of the first and second clamping members can be constructed and arranged to engage and detect shrinkage of the tissue being treated such that the first and second clamping members rotate inwardly with respect to one another.

Still further in this aspect, the first clamping member can include a first mechanical stop for limiting the rotation of the first clamping member. Similarly, the second clamping member can include a second mechanical stop for limiting the rotation of the second clamping member. Accordingly, the first and second mechanical stops can be configured to limit the rotation of the first and second clamping members when the tissue being treated achieves a pre-determined shrinkage level.

Still further in this aspect, the first clamping member can include a first jaw and a second jaw at the second end of the first clamping member. The first and second jaws of the first clamping member can be selectively adjustable to grasp the tissue being treated. Likewise, the second clamping member can include a first jaw and a second jaw at the second end of the second clamping member. The first and second jaws of the second clamping member can be selectively adjustable to grasp the tissue being treated. Furthermore, each of the first and second jaws of the first clamping member can include a textured inner surface for resistively contacting the tissue being treated. Each of the first and second jaws of the second clamping member can also include a textured inner surface for resistively contacting the tissue being treated. Additionally, each of the first and second jaws of the first clamping member can include a solution delivery channel for delivery of a conductive solution to the tissue being treated. Similarly, each of the first and second jaws of the second clamping member can include a solution delivery channel for delivery of a conductive solution to the tissue being treated.

The heat delivery modality can include a first electrode arrangement operable with the first clamping member. The first electrode arrangement can be coupled to a source of radio frequency energy. Similarly, the heat delivery modality can include a second electrode arrangement operable with the second clamping member. The second electrode arrangement can be coupled to the source of radio frequency energy. Moreover, the first electrode arrangement can include at least one wet electrode that is coupled to the source of radio frequency energy while the second electrode arrangement can include at least one wet electrode that is coupled to the source of radio frequency energy.

Further in this aspect, the electrosurgical device can include a forceps extending from the distal end of the main body between the first and second clamping members. The forceps can include a first arm and a second arm that is selectively adjustable to slidably receive the tissue being treated. In this aspect, the heat delivery modality can include a first electrode disposed at the first arm of the forceps and a second electrode disposed at the second arm of the forceps. Furthermore, both the first and second electrodes can be wet electrodes. Still further, the first arm of the forceps can include a first solution delivery channel for delivery of a conductive solution to the tissue being treated. Similarly, the second arm of the forceps can include a second solution delivery channel for delivery of a conductive solution to the tissue being treated.

The sensor arrangement can be configured to provide input to the heat delivery modality such that the thermal energy being provided by the heat delivery modality is varied according to the shrinkage of the tissue being treated. Alternatively, the thermal energy provided by the heat delivery modality can be minimized when the tissue being treated achieves a predetermined shrinkage level. Furthermore, the sensor arrangement can be operably connected to a displacement measurement device for measuring the change in shrinkage of the tissue being treated, such as, a linear potentiometer, an optical sensor, a spring/force sensor, or other measurement device.

In yet another aspect, the disclosure relates to an electrosurgical device comprising a main body having a proximal end and a distal end, a heat delivery modality situated and arranged at the distal end of the main body, and a sensor arrangement situated and arranged at the distal end of the main body. In this aspect, the heat delivery modality is capable of providing thermal energy to a tissue being treated as well as a continuous flow of electrically conductive fluid to the tissue being treated while thermal energy is introduced. The sensor arrangement is configured to engage and detect shrinkage of the tissue being treated and can comprise first and second clamping members that are situated astride the main body. In this aspect, the first clamping member can include a first end pivotably connected at the main body and a second end opposite the first end. Similarly, the second clamping member can include a first end pivotably connected at the main body and a second end opposite the first end. Each of the second ends of the first and second clamping members are preferably constructed and arranged to engage and detect shrinkage of the tissue being treated such that the first and second clamping members rotate inwardly with respect to one another.

Still further in this aspect, the first clamping member can include a first jaw and a second jaw at the second end of the first clamping member. The first and second jaws of the first clamping member can be selectively adjustable to grasp the tissue being treated. Likewise, the second clamping member can include a first jaw and a second jaw at the second end of the second clamping member. The first and second jaws of the second clamping member can be selectively adjustable to grasp the tissue being treated. Furthermore, each of the first and second jaws of the first clamping member can include a textured inner surface for resistively contacting the tissue being treated. Each of the first and second jaws of the second clamping member can also include a textured inner surface for resistively contacting the tissue being treated. Additionally, each of the first and second jaws of the first clamping member can include a solution delivery channel for delivery of a conductive solution to the tissue being treated. Similarly, each of the first and second jaws of the second clamping member can include a solution delivery channel for delivery of a conductive solution to the tissue being treated.

Still further in this aspect, the heat delivery modality can include a first electrode arrangement operable with the first clamping member and coupled to a source of radio frequency energy. Similarly, the heat delivery modality can include a second electrode arrangement operable with the second clamping member and coupled to the source of radio frequency energy. The first electrode arrangement can include at least one wet electrode that is coupled to the source of radio frequency energy. Similarly, the second electrode arrangement can include at least one wet electrode that is coupled to the source of radio frequency energy.

Further in this aspect, the electrosurgical device can include a forceps extending from the distal end of the main body between the first and second clamping members. The forceps can include a first arm and a second arm that is selectively adjustable to slidably receive the tissue being treated. In this aspect, the heat delivery modality can include a first wet electrode disposed at the first arm of the forceps and coupled to a source of radio frequency energy. Similarly, the heat delivery modality can include a second wet electrode disposed at the second arm of the forceps and coupled to a source of radio frequency energy. Still further, the first arm of the forceps can include a first solution delivery channel for delivery of a conductive solution to the tissue being treated. Similarly, the second arm of the forceps can include a second solution delivery channel for delivery of a conductive solution to the tissue being treated.

The sensor arrangement can be configured to provide input to the heat delivery modality such that the thermal energy being provided by the heat delivery modality is varied according to the shrinkage of the tissue being treated. Alternatively, the thermal energy provided by the heat delivery modality can be minimized when the tissue being treated achieves a pre-determined shrinkage level. Furthermore, the sensor arrangement can be operably connected to a displacement measurement device for measuring the change in shrinkage of the tissue being treated, such as, a linear potentiometer, an optical sensor, a spring/force sensor, or other measurement device.

BRIEF DESCRIPTION OF THE DRAWINGS

The invention may be more completely understood in consideration of the following detailed description of various embodiments of the invention in connection with the accompanying drawings, in which:

FIG. 10 illustrates an alternative configuration of the electrosurgical device of FIG. 1 for measuring change in tissue dimension in accordance with the present disclosure.

Figure 1:
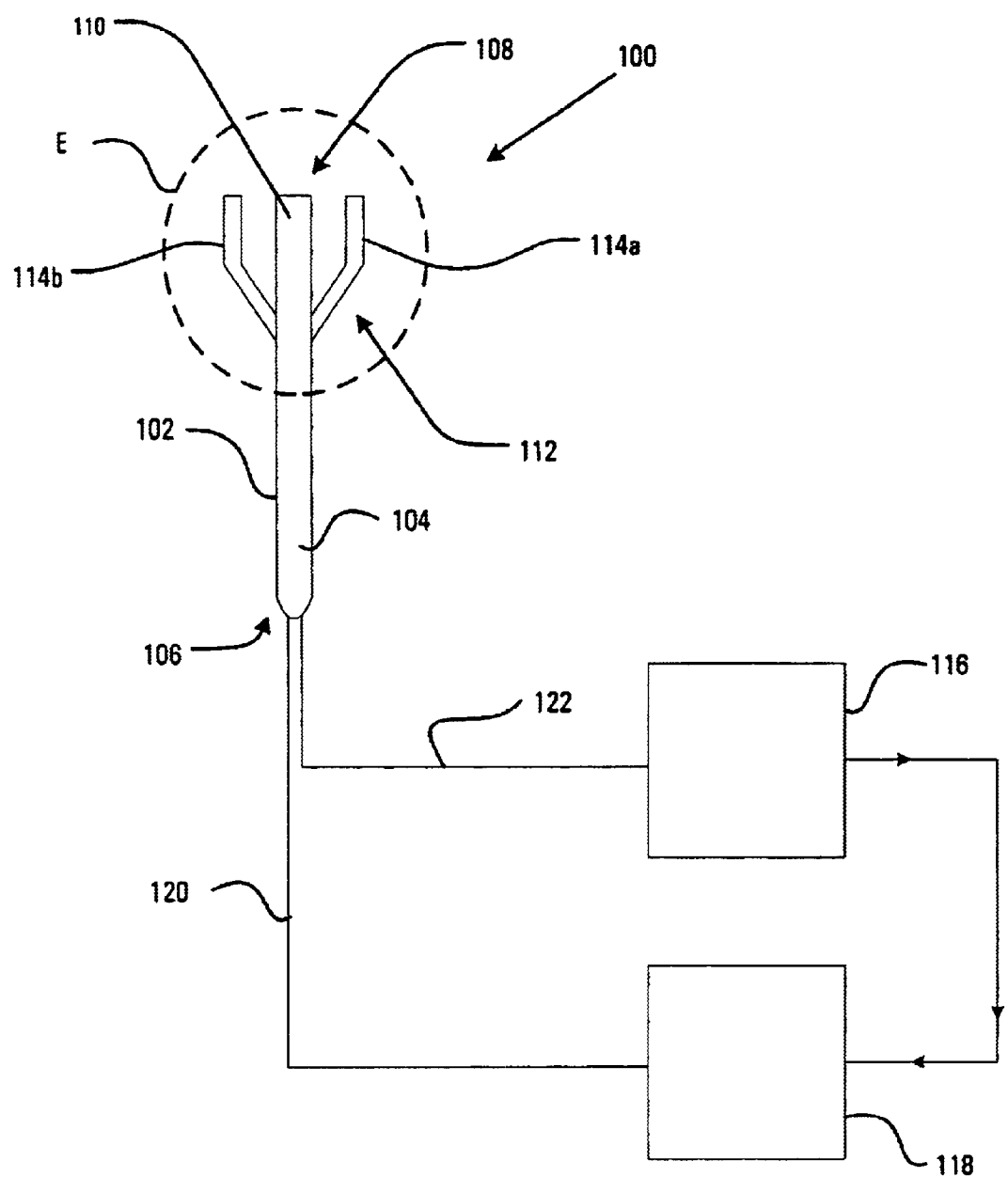
FIG. 1 is a high-level diagram illustrating one possible embodiment of an electrosurgical device having a sensor for detecting a change in tissue dimension in accordance with the present disclosure connected to a power source and an electronic controller.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Various embodiments of the present invention will be described in detail with reference to the drawings, wherein like reference numerals represent like parts and assemblies throughout the several views. Reference to various embodiments does not limit the scope of the present invention, which is limited only by the scope of the claims attached hereto.

The following discussion is intended to provide a brief, general description of a suitable medical device for precisely measuring and/or controlling a change in tissue dimension during surgical applications. As will become apparent from the discussion below in connection with the accompanying drawings, the present disclosure has particularized applicability to electrosurgical devices having a tissue reduction or shrinkage sensor. However, it will be appreciated by those having skill in the art that the present disclosure is not limited to the specific embodiments discussed below. Rather, the medical device of the present disclosure may be implemented during any surgical procedure where thermal energy is being used to contract and/or expand collagen and it is desirous to precisely measure and/or control the change in dimension of the tissue being treated. By "change in dimension," it is generally meant that the electrosurgical device of the present disclosure is able to measure and/or control the shortening, lengthening, widening, thinning, or other similar dimensional variations, of the tissue being treated.

Now referring to FIG. 1, a medical device or electrosurgical device 100 for use during surgical procedures in accordance with the principles of the present disclosure is shown. The electrosurgical device 100 generally includes a main body 102 having a proximal end 106 and a distal end 108. The phrase "proximal end" is generally meant to refer to the portion of the electrosurgical device 100 that is held in the operator's hand during use. Conversely, the phrase "distal end" is generally meant to refer to the portion of the electrosurgical device 100 at or near a location that contacts the patient. The main body 102 can include a handle portion 104 at or near its proximal end 106 and an end effector region E at or near its distal end 108. In the illustrated embodiment, the handle portion 104 depends downwardly along the main body portion 102 away from the end effector region E to provide a suitable area for gripping or handling the electrosurgical device 100 during use. By "downwardly," it is generally meant that in the orientation shown in FIG. 1, the handle portion 104 extends below the end effector region E.

As shown in FIG. 1, the electrosurgical device 100 is connected to a power source 118 via a pair of conductors 120. The power source 118 supplies energy to the electrosurgical device 100. Furthermore, as shown in the illustrated embodiment, the electrosurgical device 100 can be configured to provide feedback to an electronic controller 116 that is configured to modulate the energy supplied by the power source 118.

The end effector region E generally includes an arrangement for delivering thermal energy to the tissue (not shown) being treated. In the embodiments illustrated in the accompanying drawings, the arrangement for delivering thermal energy can comprise a heat delivery modality 110 capable heating the tissue being treated, thereby, causing the tissue to contract. However, as discussed above, one skilled in the art will readily appreciate that the arrangement for delivering thermal energy can comprise a device capable of cooling the tissue being treated, thereby, causing the tissue to expand. The heat delivery modality 110 generally can include any mechanism capable of delivering thermal energy to the tissue being treated, such as, RF energy, microwave energy, coherent (e.g., laser) and incoherent light energy, direct thermal transfer, electrical resistive heating, as well as other similar forms of energy. One skilled in the art will readily appreciate that the heat delivery modality 118 can be connected to any suitable energy source capable of introducing thermal energy to the tissue being treated, thereby, causing the tissue to contract.

In addition to the heat delivery modality 110, the end effector region E also includes a sensor arrangement 112. The sensor arrangement 112 generally can include any device capable of engaging and detecting a change in dimension, such as, shrinkage or expansion, of the tissue (not shown) being treated as thermal energy is introduced. For example, the sensor arrangement 112 can include at least one contact sensor situated and arranged at the distal end 108 of the main body 102. While many embodiments of the sensor arrangement 112 are contemplated, the sensor arrangement illustrated in FIG. 1, generally includes a first contact sensor 114a and a second contact sensor 114b, such as, clamping members, needles, or other devices, configured to grasp or embed within the tissue being treated. One or both of the contact sensors 114a, 114b can be pivotably attached to the main body 102 of the electrosurgical device 100 such that the contact sensors 114a, 114b move relative to the change in dimension of the tissue being treated. For example, in the illustrated embodiment, the contact sensors 114a, 114b move relative to the shrinkage of the tissue being treated. As a result, the sensor arrangement 112 is able to detect the shrinkage of the tissue being treated, thereby, allowing the surgeon or operator to precisely shrink or contract the tissue being treated.

For example, in one embodiment, the surgeon or operator can precisely shrink or contract the tissue by manually adjusting the power source 118 when the tissue shrinks to a desired level. Alternatively, as discussed above, the electrosurgical device 100 can be configured to provide a feedback control signal to the electronic controller 116 that is configured to modulate the energy supplied by the power source 118 such that the electrosurgical device 100 can automatically shrink or contract the tissue being treated to a predetermined level. The predetermined level can be established according to preset criteria, such as, shrinkage percentage or total tissue length reduction. Specific embodiments of the heat delivery modality 110 and the sensor arrangement 112 will be discussed in greater detail below.

Figure 2:
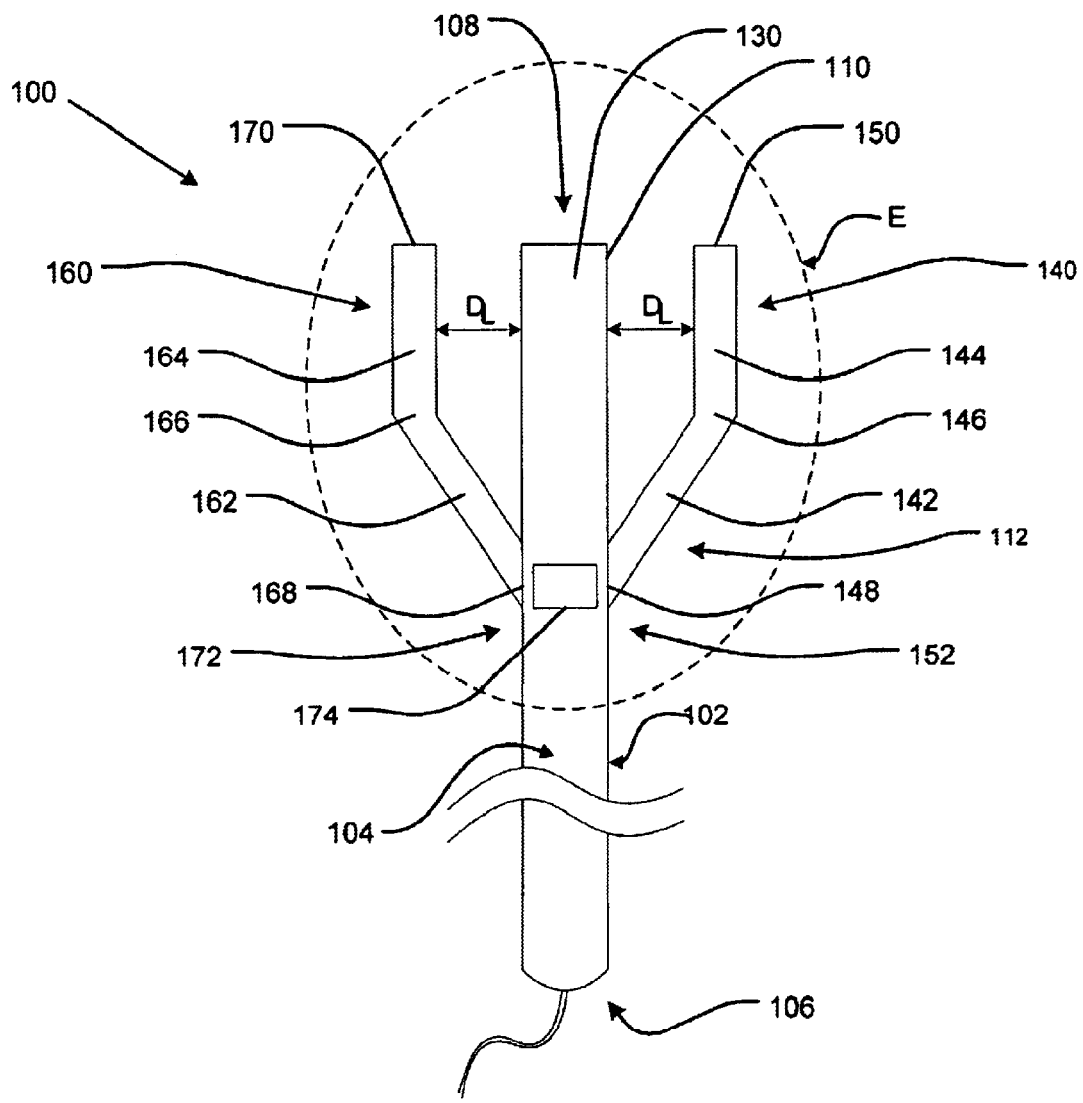
FIG. 2 is an enlarged, top view illustrating the electrosurgical device of FIG. 1 having a sensor for detecting a change in tissue dimension.
Figure 3:
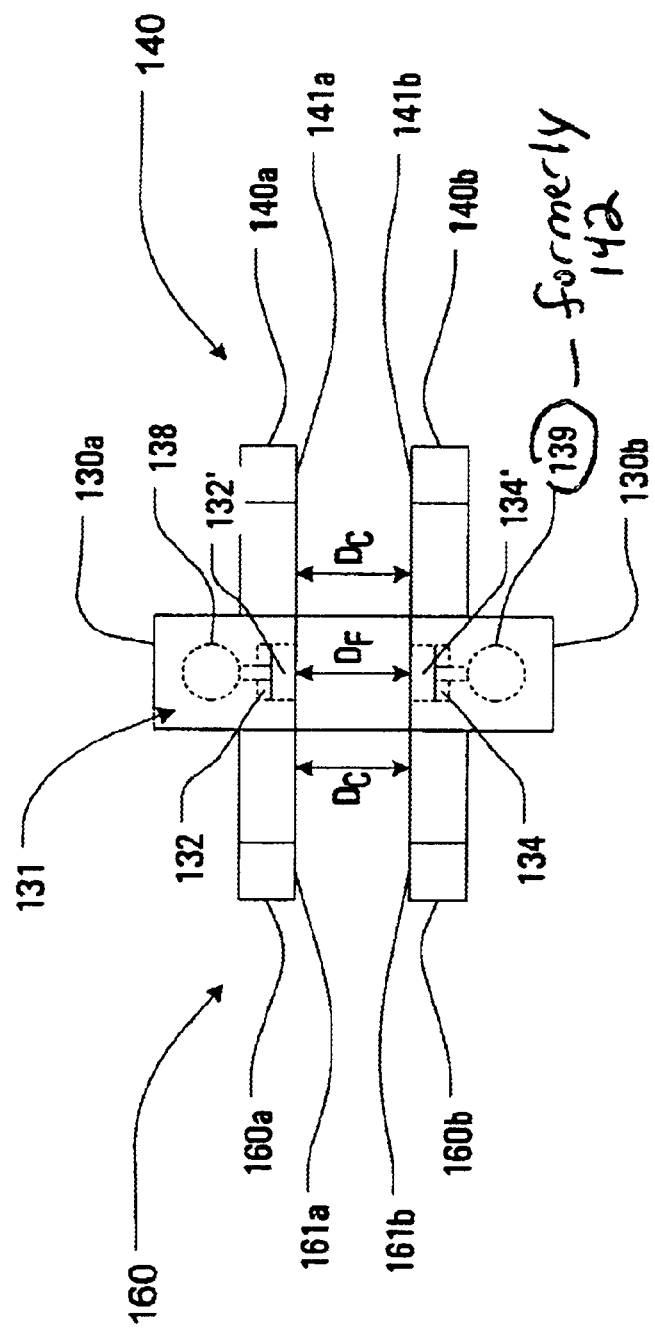
FIG. 3 is an enlarged, side section view illustrating the electrosurgical device of FIG. 2 having a sensor for detecting a change in tissue dimension.

A first embodiment of an electrosurgical device 100 for use in accordance with the principles of the present disclosure will now be described in connection with FIGS. 2–5. As shown in FIGS. 2 and 3, the end effector region E can include a forceps 130 for receiving the target tissue (not shown) to be treated. As shown in FIG. 3, the forceps 130 includes a first arm 130a and a second arm 130b. In the illustrated embodiment, the first and second arms 130a, 130b are spaced apart a distance $D_F$ to define a passageway therebetween. Preferably, the forceps 130 slidably receive the target tissue to be treated within the passageway defined between the first and second arms 130a, 130b. By "slidably receive," it is generally meant that the distance $D_F$ can be selectively adjusted such that the first and second arms 130a, 130b of the forceps 130 maintain slidable contact with and do not restrict the movement of the target tissue to be treated when it is received within the passageway. Thus, the forceps 130 allow the tissue being treated to shrink as thermal energy is introduced to the treatment zone.

The forceps 130 define a heat delivery modality 110 for providing thermal energy to the tissue (not shown) being treated. While many embodiments of the heat delivery modality 110 are contemplated, in the illustrated embodiment, the heat delivery modality 110 defined by the forceps 130 includes an electrode arrangement 131 for providing thermal energy to the tissue being treated. In particular, as shown in FIG. 3, the first arm 130a of the forceps 130 can include a first electrode 132, and the second arm 130b can include a second electrode 134 having a polarity opposite the first electrode 132. The electrode arrangement 131 illustrated in FIG. 3 is a bipolar configuration. However, one skilled in the art will readily appreciate that the electrosurgical device 100 of the present disclosure can be implemented using a monopolar electrode arrangement.

In one possible embodiment, the first and second electrodes 132, 134 can be selectively energized to provide thermal energy to the tissue being treated. In a preferred embodiment, the thermal energy supplied to the tissue being treated is produced as a result of a voltage gradient created by a RF energy power source 118 (FIG. 1). However, it will be appreciated that the thermal energy supplied to the tissue being treated can be provided by any suitable energy source sufficient to allow the tissue being treated to shrink or contract. For example, as discussed above, the energy source 118 connected to the heat delivery modality 131 can be microwave energy, coherent (e.g., laser) or incoherent light energy, direct thermal transfer, electrical resistive heating, as well as other similar forms or sources of energy.

Preferably, the electrode arrangement 131 discussed above is a wet electrode arrangement and is used in conjunction with a conductive fluid (e.g., an electrolytic solution). The use of a conductive fluid in connection with the electrode arrangement 131 allows the thermal energy to be distributed equally, thereby, minimizing hot spots within the tissue being treated. In the embodiment illustrated in FIG. 3, the first arm 130a of the forceps 130 (FIG. 2) is provided with a solution delivery channel 138. Similarly, the second arm 130b is provided with a solution delivery channel 139. The solution delivery channels 138, 139 provide a path for fluid communication between a fluid source (not shown) and the forceps 130. In particular, the solution delivery channel 138 provides a path for fluid communication between a fluid source and the first arm 130a and the solution delivery channel 139 provides a path for fluid communication between a fluid source and the second arm 130b. Fluid can flow from the solution delivery channel 138 through small holes (not shown) in the first electrode 132 and into a region 132' located between the first electrode 132 and the tissue (not shown). Similarly, fluid can flow from the solution delivery channel 139 through small holes (not shown) in the second electrode 134 and into a region 134' located between the second electrode 134 and the tissue. In so doing, the electrosurgical device 100 can introduce a conductive fluid, such as, a saline solution or other similar electrolytic solution, at the electrode/tissue interface to minimize the amount of tissue damage, char formation, smoke generation or other similar damage to the tissue being treated.

In addition to the heat delivery modality 110, the end effector region E also includes a sensor arrangement 112 configured to engage and detect a change in dimension of the tissue being treated. For example, in the illustrated embodiment, the sensor arrangement 112 can be used to measure the shrinkage or contraction of the tissue being treated. The sensor arrangement 112 generally includes at least one contact sensor situated and arranged at the distal end 108 of the main body 102. Exemplary contact sensors capable of engaging and detecting shrinkage of the tissue being treated include, but are not limited to, clamping members, needles, or other devices that can grasp or embed within the tissue being treated. While many embodiments of the sensor arrangement 112 are contemplated, in the illustrated embodiment, the sensor arrangement 112 includes a first clamp 140 and a second clamp 160 situated and arranged astride the forceps 130. By "astride," it is generally meant that the forceps 130 is situated and arranged between the first and second clamps 140, 160.

As shown in FIG. 3, the first clamp 140 can comprise first and second symmetrical jaw members 140a, 140b. Each of the jaw members 140a, 140b include a lower arm member 142 (FIG. 2) extending away from the main body portion 102 of the device 100 and an upper flange member 144 (FIG. 2). In this embodiment, an elbow or shoulder 146 (FIG. 2) is defined by the intersection of the lower arm member 142 and the upper flange 144. The first and second symmetrical jaw members 140a, 140b also include a proximal end portion 148 (FIG. 2) and a distal end portion 150 (FIG. 2). The phrase "proximal end portion" is generally meant to refer to the portion of each of the first and second jaw members 140a, 140b at or near their point of attachment to the main body 102. Likewise, the phrase "distal end portion" is generally meant to refer to the portion of each of the first and second jaw members 140a, 140b at or near a location furthest from their point of attachment to the main body 102.

Similarly, the second clamp 160 comprises first and second symmetrical jaw members 160a, 160b. Each of the jaw members 160a, 160b include a lower arm member 162 (FIG. 2) extending away from the main body portion 102 of the device 100 and an upper flange member 164 (FIG. 2). In this embodiment, an elbow or shoulder 166 (FIG. 2) is defined by the intersection of the lower arm member 162 and the upper flange 164. Each of the jaw members 160a, 160b comprising the second clamp 160 also include a proximal end portion 168 (FIG. 2) and a distal end portion 170 (FIG. 2). As with the first clamp 140 discussed above, the phrase "proximal end portion" is generally meant to refer to the portion of each of the first and second jaw members 160a, 160b at or near their point of attachment to the main body 102. Similarly, the phrase "distal end portion" is generally meant to refer to the portion of each of the jaw members 160a, 160b at or near a location furthest from their point of attachment to the main body 102.

In the illustrated embodiment, the first and second symmetrical jaw members 140a, 140b comprising the first clamp 140 are spaced apart a distance $D_c$ to define a passageway for receiving the tissue being treated. In one possible embodiment, the distance $D_c$ can be selectively adjusted, thereby, increasing or decreasing the compressive forces being applied to the tissue being treated. Moreover, the first and second jaw members 140a, 140b can include inner surfaces 141a, 141b, respectively, that resistively contact the tissue being treated. By "resistively contact," it is generally meant that the inner surfaces 141a, 141b are textured such that the first clamp 140 can maintain a grasp on the tissue being treated. For example, the inner surfaces 141a, 141b can include serrations, grooves, or any other surface roughness that increase the friction between the first clamp 140 and the tissue being treated.

Similarly, the first and second symmetrical jaw members 160a, 160b comprising the second clamp 160 are spaced apart a distance $D_c$ to define a passageway for receiving the tissue being treated. As discussed above in connection with the first clamp 140, in one possible embodiment, the distance $D_c$ can be selectively adjusted to increase or decrease the compressive forces being applied to the tissue being treated. Moreover, the first and second jaw members 160a, 160b comprising the second clamp 160 can include inner surfaces 161a, 161b that resistively contact the tissue being treated. By "resistively contact," it is generally meant that the inner surfaces 161a, 161b are textured such that the second clamp 160 maintains a grasp on the tissue being treated. For example, the inner surfaces 161a, 161b can include serrations, grooves, or any other similar surface roughness that increase the friction between the second clamp 160 and the tissue being treated.

Figure 4:
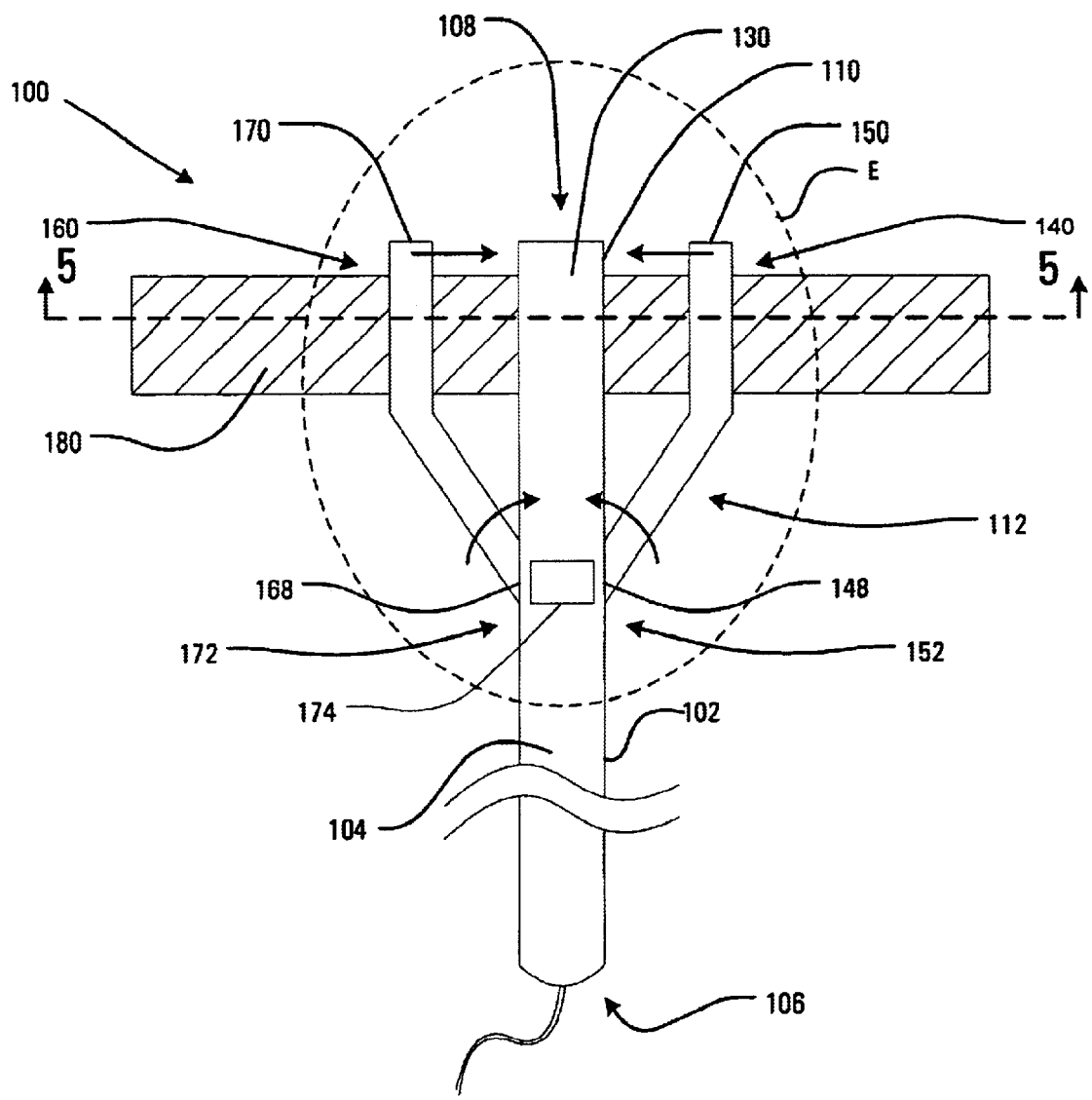
FIG. 4 is an enlarged, a top view illustrating the electrosurgical device of FIG. 2 having a tissue positioned within the device.
Figure 5:
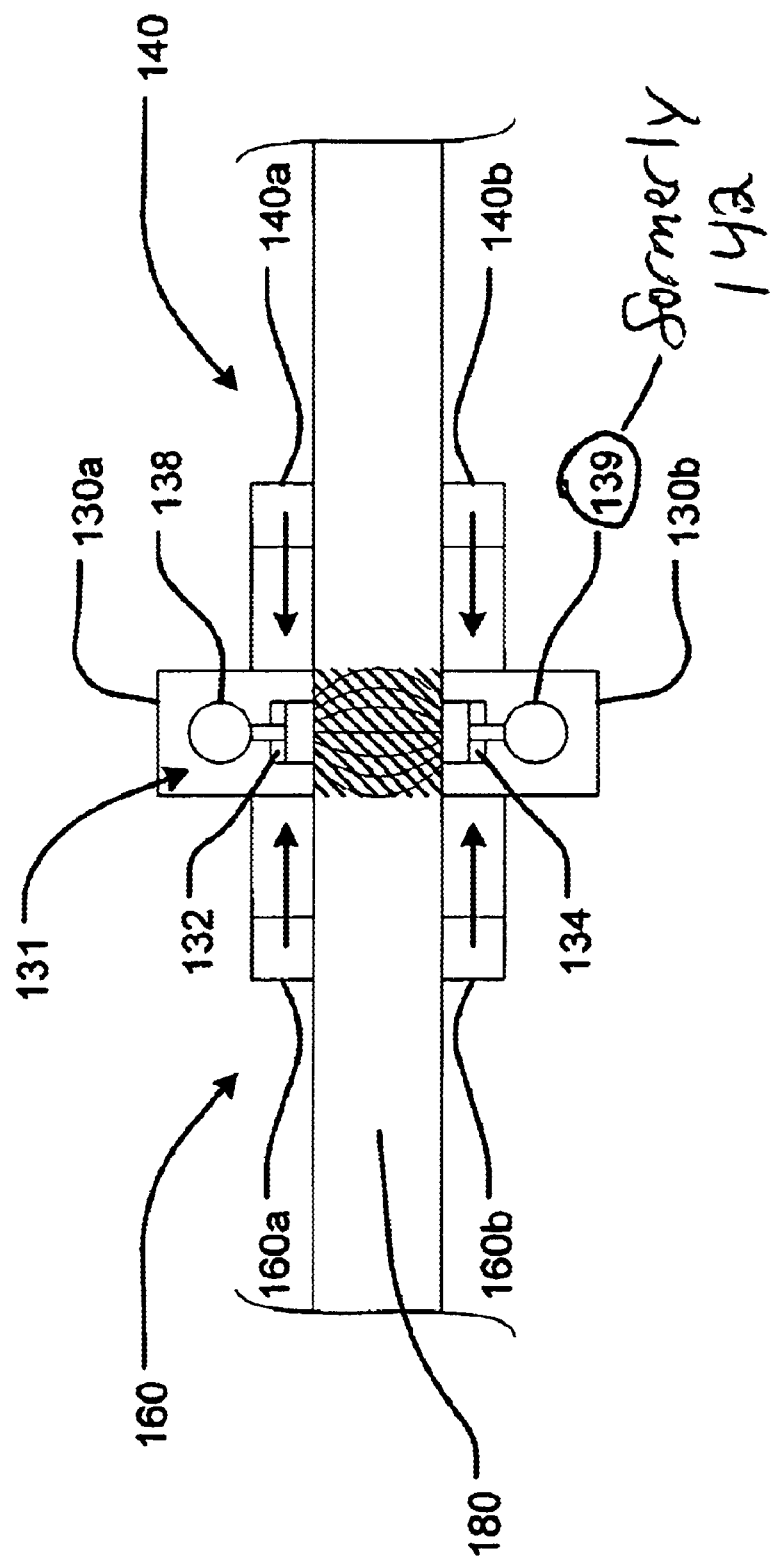
FIG. 5 is an enlarged, side section view illustrating the electrosurgical device of FIG. 4.

Now in reference to FIGS. 4 and 5, a tissue 180, such as, a tendon or ligament is shown positioned between the forceps 130 and the first and second clamps 140, 160 of the electrosurgical device 100. More particularly, the tissue 180 is shown positioned between the first and second arms 130a, 130b of the forceps 130. Similarly, the tissue 180 is shown positioned between the first and second jaws 140a, 140b of the first clamp 140 and the first and second jaws 160a, 160b of the second clamp 160. As discussed above, the operator of the electrosurgical device 100 can selectively energize the heat delivery modality 110 to provide thermal energy to the tissue treatment zone. In the illustrated embodiment, the operator of the electrosurgical device 100 can selectively energize the electrode arrangement 131 (e.g., the first and second electrodes 132, 134) to induce an electric current through the tissue 180 being treated or, more particularly, the treatment zone. As used herein, the phrase "treatment zone" generally refers to the portion or area of the tissue 180 located adjacent to and/or substantially between the first and second arms 130a, 130b of the forceps 130. In the illustrated embodiment, the thermal energy passes through the treatment zone as shown by the dotted lines in FIG. 5.

The thermal energy causes the tissue 180 within the treatment zone to contract or shrink. As discussed above, it is typically desirable to allow the surgeon or operator of the electrosurgical device 100 to control the shrinkage of the tissue 180. Existing electrosurgical devices monitor the temperature at or near the treatment zone to allow the surgeon to control the thermal energy introduced to the tissue treatment zone. The electrosurgical device 100 of the present disclosure, however, allows the operator to precisely control the thermal energy being introduced to the tissue treatment zone by monitoring the shrinkage of the tissue 180 being treated. Accordingly, the shrinkage of the tissue 180 being treated can be more precisely controlled.

To accomplish this, the sensor arrangement 112 is configured to engage or contact the tissue 180, thereby, sensing or detecting the shrinkage or contraction of the tissue 180 as thermal energy is introduced to the tissue treatment zone. For example, in the illustrated embodiment, the first and second clamping members 140, 160 are shown in engagement with the tissue 180 outside of the tissue treatment zone. In this embodiment, the first clamp 140 is preferably pivotably connected to the main body 102 at or near a pivot position 152. As a result, the first clamp 140 is able to rotate about the pivot position 152 such that the upper flange 144 (FIG. 2) moves inwardly towards the forceps 130. By "inwardly," it is generally meant that the first clamp 140 moves leftward and towards the forceps 130 such that the lateral distance $D_L$ (FIG. 2) between the first clamp 140 and the forceps 130 is reduced. Similarly, the second clamp 160 is preferably pivotably connected to the main body 102 at or near a pivot position 172. As a result, the second clamp 160 is able to rotate about the pivot position 172 such that the upper flange 164 moves inwardly towards the forceps 130. By "inwardly," it is generally meant that in the orientation shown in FIG. 2, the second clamp 160 moves rightward and towards the forceps 130 such that the lateral distance $D_L$ (FIG. 2) between the second clamp 160 and the forceps 130 is reduced. While the first and second clamps 140, 160 are pivotably connected to the main body 102, one skilled in the art will readily appreciate that the first and second clamps 140, 160 can be slidably connected to the main body 102 so that they are able to slide back and forth relative to the expansion and/or contraction of the tissue 180 being treated.

As a result of this configuration, the electrosurgical device 100 is able to detect a change in dimension of the tissue 180 being treated as thermal energy is introduced to the treatment zone. In particular, in the illustrated embodiment, the electrosurgical device 100 is able to detect the shrinkage or contraction of the tissue 180 being treated as thermal energy is introduced to the treatment zone. Furthermore, the electrosurgical device 100 is able to detect the recovery or expansion of the tissue 180 being treated as the thermal energy (e.g., heat) is removed from the treatment zone. In a preferred embodiment, the electrosurgical device 100 also can include a displacement measurement device 174 for measuring the change in dimension of the tissue 180, for example, the shrinkage or contraction of the tissue 180 being treated. In particular, in the illustrated embodiment, the first and second clamps 140, 160 are coupled to a displacement measurement device 174 that measures the angular or rotational displacement of the first and second clamps 140, 160 as thermal energy is introduced to the treatment zone. For example, the first and second clamps 140, 160 can be coupled to a linear potentiometer, optical sensor, spring/force sensor, or other similar displacement measurement device for measuring the angular or rotation displacement of the first and second clamps 140, 160.

The amount of change in the dimension of the tissue 180 being treated can be determined by calculating the displacement of each of the contact sensors used to engage the tissue 180. In the illustrated embodiment, the amount of shrinkage in the tissue 180 is determined by calculating the angular displacement of the first and second clamps 140, 160. Once the desired shrinkage of the tissue 180 has been achieved, the displacement measurement device 174 can provide a control signal to the electronic control unit 116 (FIG. 1) to reduce or minimize the amount of thermal energy being supplied to the treatment zone by regulating the power source 118 (FIG. 1). Alternatively, the first and second clamps 140, 160 can include a mechanical stop (not shown) to prevent shrinkage of the tissue beyond a pre-determined amount or percentage.

Figure 6:
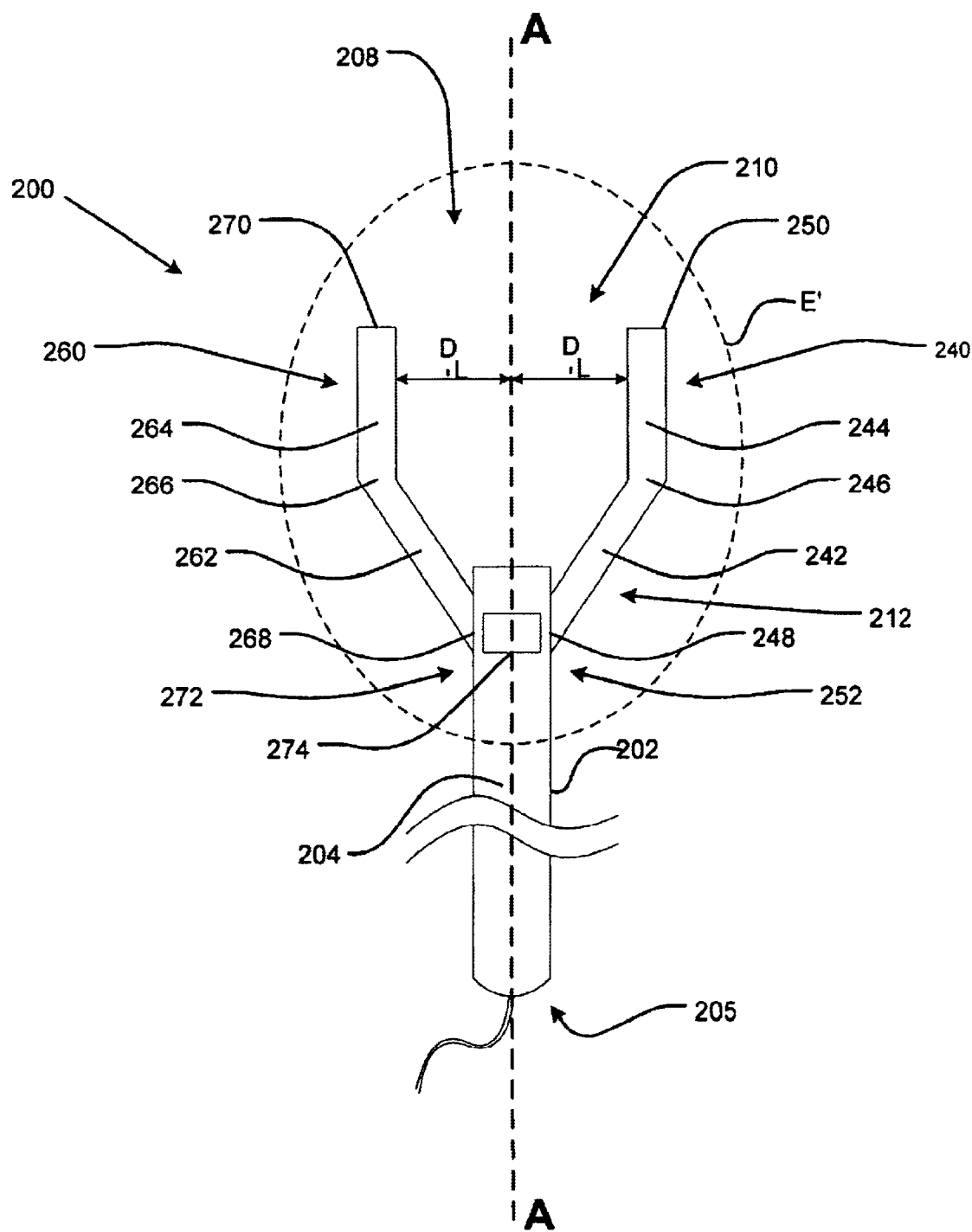
FIG. 6 is an enlarged, top view illustrating a second possible embodiment of the electrosurgical device of FIG. 1.

A second possible embodiment of a medical device for use in accordance with the principles of the present disclosure will now be described in connection with FIGS. 6–9. As shown in FIG. 6, the electrosurgical device 200 generally includes a main body 202 having a proximal end 206 and a distal end 208. The phrase "proximal end" is generally meant to refer to the portion of the electrosurgical device 200 that is held in the operator's hand during use. Conversely, the phrase "distal end" is generally meant to refer to the portion of the electrosurgical device 200 at or near a location that contacts the patient. The main body 202 can include a handle portion 204 at or near its proximal end 206 and an end effector region E' at or near its distal end 208. In the illustrated embodiment, the handle portion 204 depends downwardly along the main body portion 202 away from the end effector region E' to provide a suitable area for gripping or handling the electrosurgical device 200 during use. By "downwardly," it is generally meant that in the orientation shown in FIG. 5, the handle portion 204 extends below the end effector region E'.

In this embodiment, the end effector region E' includes a sensor arrangement 212 that is configured to engage and detect a change in dimension of the tissue being treated. The sensor arrangement 212 generally includes at least one contact sensor situated and arranged at the distal end 208 of the main body 202. Exemplary contact sensors capable of engaging and detecting a change in dimension of the tissue being treated include, but are not limited to, clamping members, needles, or other devices that can grasp or embed within the tissue being treated. While many embodiments of the sensor arrangement 212 are contemplated, in the illustrated embodiment, the sensor arrangement 212 includes a first clamp 240 and a second clamp 260 situated and arranged astride the main body 202.

Figure 7:
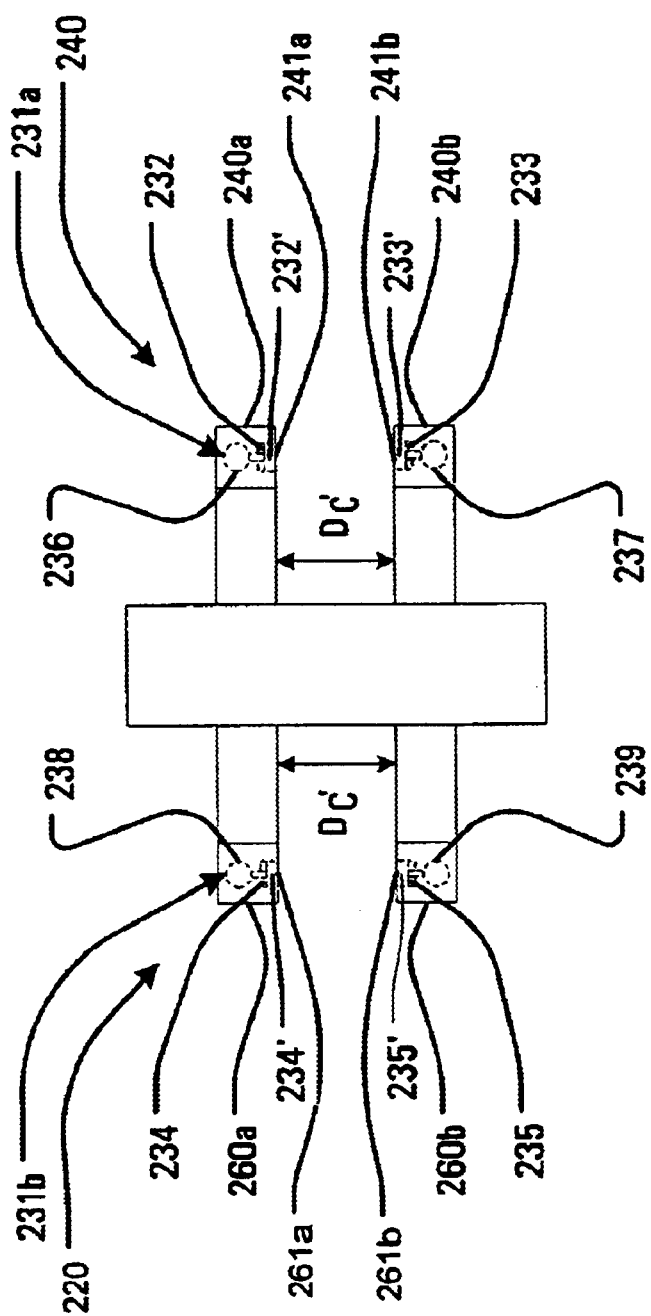
FIG. 7 is an enlarged, side section view illustrating the electrosurgical device of FIG. 6 having a sensor for detecting a change in tissue dimension.

As shown in FIG. 7, the first clamp 240 can comprise first and second symmetrical jaw members 240a, 240b. Each of the jaw members 240a, 240b include a lower arm member 242 (FIG. 6) extending away from the main body portion 202 of the device 200 and an upper flange member 244 (FIG. 6). In this embodiment, an elbow or shoulder 246 (FIG. 6) is defined by the intersection of the lower arm member 242 and the upper flange 244. The first and second symmetrical jaw members 240a, 240b also include a proximal end portion 248 (FIG. 6) and a distal end portion 250 (FIG. 6). The phrase "proximal end portion" is generally meant to refer to the portion of each of the first and second jaw members 240a, 240b at or near their point of attachment to the main body 202. Likewise, the phrase "distal end portion" is generally meant to refer to the portion of each of the first and second jaw members 240a, 240b at or near a location furthest from their point of attachment to the main body 202.

Similarly, the second clamp 260 can comprise first and second symmetrical jaw members 260a, 260b. Each of the jaw members 260a, 260b include a lower arm member 262 (FIG. 6) extending away from the main body portion 202 of the device 200 and an upper flange member 264 (FIG. 6). In this embodiment, an elbow or shoulder 266 (FIG. 6) is defined by the intersection of the lower arm member 262 and the upper flange 264. Each of the jaw members 260a, 260b comprising the second clamp 260 also include a proximal end portion 268 (FIG. 6) and a distal end portion 270 (FIG. 6). As with the first clamp 240 discussed above, the phrase "proximal end portion" is generally meant to refer to the portion of the second clamp 260 at or near it point of attachment to the main body 202. Similarly, the phrase "distal end portion" is generally meant to refer to the portion of each of the jaw members 260a, 260b at or near a location furthest from its point of attachment to the main body 202.

In the illustrated embodiment, the first and second symmetrical jaw members 240a, 240b comprising the first clamp 240 are spaced apart a distance $D_c'$ to define a passageway for receiving the tissue being treated. In one possible embodiment, the distance $D_c'$ can be selectively adjusted, thereby, increasing or decreasing the compressive forces being applied to the tissue being treated. Moreover, the first and second jaw members 240a, 240b can include inner surfaces 241a, 241b that resistively contact the tissue being treated. By "resistively contact," it is generally meant that the inner surfaces 241a, 241b are textured such that the first clamp 240 maintains a grasp on the tissue being treated. For example, the inner surfaces 241a, 241b can include serrations, grooves, or any other similar surface roughness that increase the friction between the first clamp 240 and the tissue being treated.

Similarly, the first and second symmetrical jaw members 260a, 260b comprising the second clamp 260 are spaced apart a distance $D_c'$ to define a passageway for receiving the tissue being treated. As discussed above in connection with the first clamp 240, in one possible embodiment, the distance $D_c'$ can be selectively adjusted to increase or decrease the compressive forces being applied to the tissue being treated. Moreover, the first and second jaw members 260a, 260b comprising the second clamp 260 can include inner surfaces 261a, 261b that resistively contact the tissue being treated. By "resistively contact," it is generally meant that the inner surfaces 261a, 261b are textured such that the second clamp 260 maintains a grasp on the tissue being treated. For example, the inner surfaces 261a, 261b can include serrations, grooves, or any other surface roughness that increase the friction between the second clamp 260 and the tissue being treated.

As with the first embodiment discussed above, the end effector region E' includes a heat delivery modality 210 for providing thermal energy to the tissue being treated. While many embodiments of the heat delivery modality 210 are contemplated, in the illustrated embodiment, the heat delivery modality 210 includes an electrode arrangement for providing thermal energy to the tissue being treated. In particular, as shown in FIG. 7, the heat delivery modality 210 can include a first electrode arrangement 231a operable with the first clamp 240 and a second electrode arrangement 231b operable with the second clamp 260. The first electrode arrangement 231a includes a first electrode 232 at the first jaw member 240a of the first clamp 240 and a second electrode 233 at the second jaw member 240b. Similarly, the second electrode arrangement 231b includes a first electrode 234 at the first jaw member 260a of the second clamp 260 and a second electrode 235 at the second jaw member 260b. In one possible embodiment, the first and second electrodes 232, 233 at the first clamp 240 and the first and second electrodes 234, 235 at the second clamp 260 can be selectively energized to provide electrical energy to the tissue being treated. In a preferred embodiment, the thermal energy provided to the tissue being treated is RF energy.

In the embodiment illustrated in FIG. 7, the first and second jaw members 240a, 240b of the first clamp 240 is preferably provided with a solution delivery channel. In particular, a first solution delivery channel 236 is provided within the first jaw member 240a and a second solution delivery channel 237 is provided within the second jaw member 240b. The solution delivery channels 236, 237 provide a path for fluid communication between a fluid source (not shown) and the first clamp 240. Specifically, the solution delivery channel 236 provides a path for fluid communication between a fluid source and the first jaw member 240a and the solution delivery channel 237 provides a path for fluid communication between a fluid source and the second jaw member 240b. Fluid can flow from the solution delivery channel 236 through small holes (not shown) in the first electrode 232 (at the first clamp 240) and into a region 232' located between the first electrode 232 and the tissue (not shown). Similarly, fluid can flow from the solution delivery channel 237 through small holes (not shown) in the second electrode 233 (at the first clamp 240) and into a region 233' located between the second electrode 233 and the tissue.

Similarly, the first and second jaw members 260a, 260b of the second clamp 260 is preferably provided with a solution delivery channel. In particular, a first solution delivery channel 238 is provided within the first jaw member 260a and a second solution delivery channel 239 is provided within the second jaw member 260b. The solution delivery channels 238, 239 provide a path for fluid communication between a fluid source (not shown) and the second clamp 260. Specifically, the first solution delivery channel 238 provides a path for fluid communication between a fluid source and the first jaw member 260a and the second solution delivery channel 239 provides a path for fluid communication between a fluid source and the second jaw member 260b. Fluid can flow from the solution delivery channel 238 through small holes (not shown) in the first electrode 234 (at the second clamp 260) and into a region 234' located between the first electrode 234 and the tissue (not shown). Similarly, fluid can flow from the solution delivery channel 239 through small holes (not shown) in the second electrode 235 (at the second clamp 260) and into a region 235' located between the second electrode 233 and the tissue. In providing the solution delivery channels 236, 237, 238, 239, the electrosurgical device 200 of the present disclosure is able to introduce a conductive fluid, such as, a saline solution or other similar electrolytic solution, at the electrode/tissue interface to minimize the amount of tissue damage, char formation, smoke generation or other similar damage to the tissue being treated.

Figure 8:
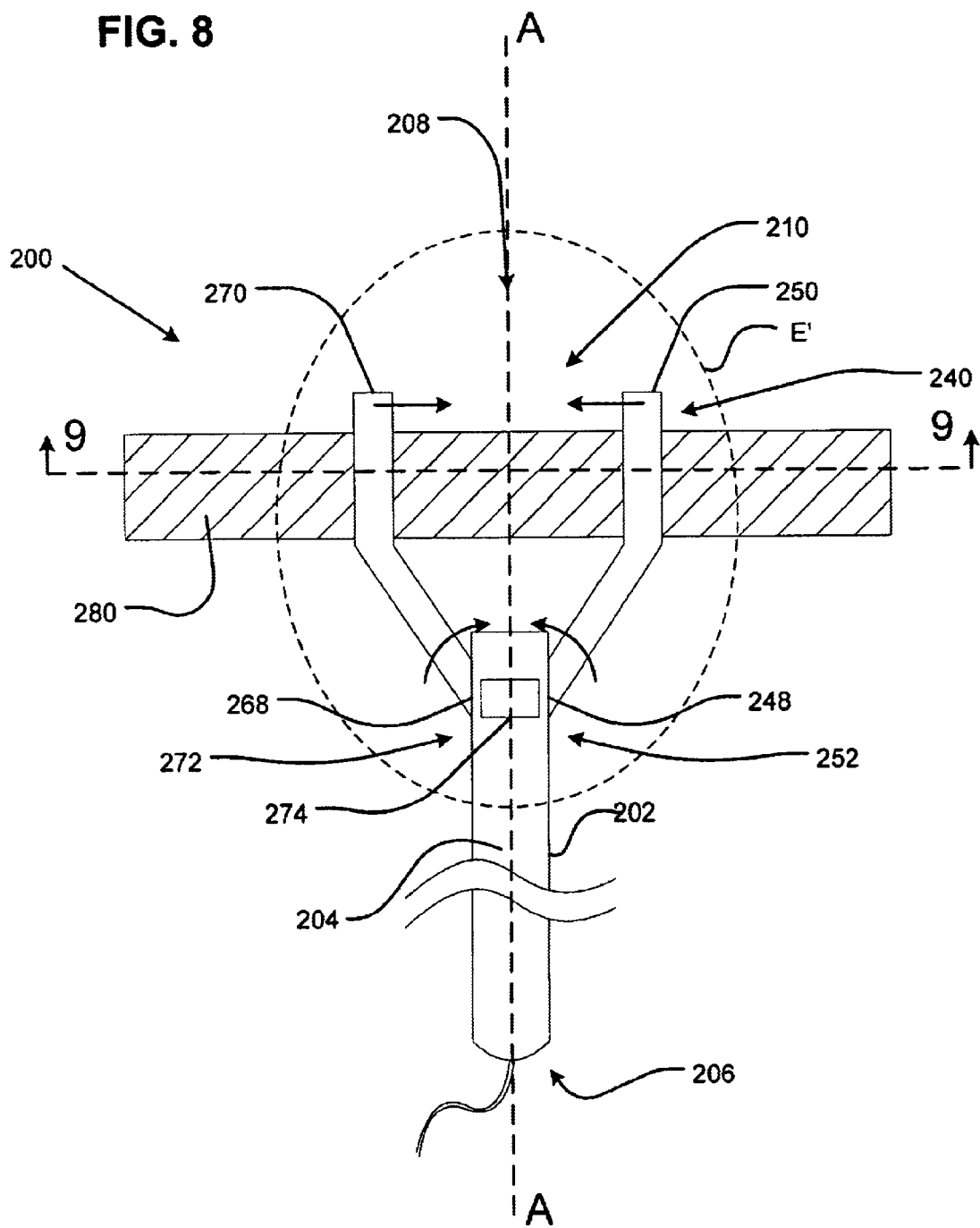
FIG. 8 is an enlarged, a top view illustrating the electrosurgical device of FIG. 6 having a tissue positioned within the device.
Figure 9:
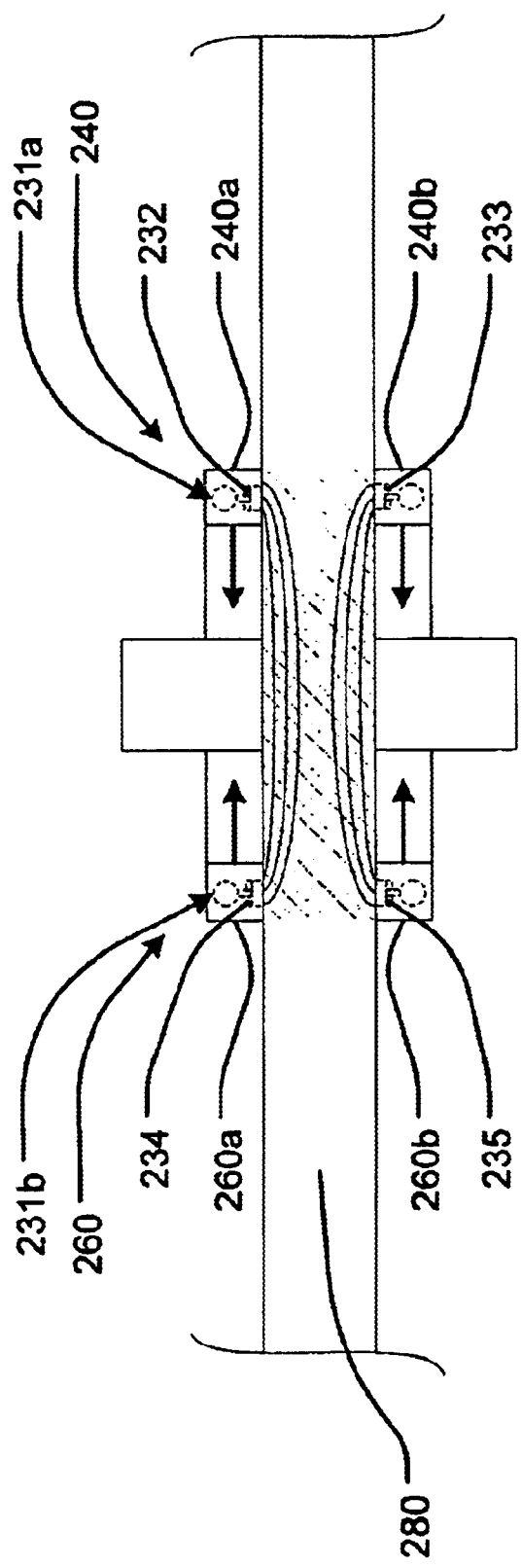
FIG. 9 is an enlarged, side section view illustrating the electrosurgical device of FIG. 8.

Now in reference to FIGS. 8 and 9, a tissue 280 such as, a tendon or ligament is shown positioned between the first and second clamps 240, 260 of the electrosurgical device 200. More particularly, the tissue 280 is shown positioned between the first and second jaws 240a, 240b of the first clamp 240 and the first and second jaws 260a, 260b of the second clamp 260. As discussed above, the operator of the electrosurgical device 200 can selectively energize the first and second electrodes 232, 233 situated at the first clamp 240 and the first and second electrode 234, 235 situated at the second clamp 260 to provide thermal energy to the tissue 280 being treated or, more particularly, the treatment zone. As used herein, the phrase "treatment zone" generally refers to the portion or area of the tissue 280 located adjacent to and/or substantially between the first and second clamps 240, 260. In the illustrated embodiment, thermal energy passes through the treatment zone as shown by the dashed lines in FIG. 9.

The thermal energy causes the tissue 280 within the treatment zone to contract or shrink. As with the first embodiment disclosed above, the electrosurgical device 200 allows the operator to precisely control the thermal energy being introduced to the tissue treatment zone by monitoring the shrinkage of the tissue 280 being treated. Accordingly, the shrinkage of the tissue 280 can be more precisely controlled.

To accomplish this, the sensor arrangement 212 is configured to engage or contact the tissue 280, thereby, sensing or detecting the shrinkage or contraction of the tissue 280 as thermal energy is introduced to the treatment zone. For example, in the illustrated embodiment, the first and second clamping members 240, 260 are shown in engagement with the tissue 280. In this embodiment, the first clamp 240 is preferably pivotably connected to the main body 202 at or near a pivot position 252. As a result, the first clamp 240 is able to rotate about the pivot 252 such that the upper flange 244 (FIG. 6) moves inwardly towards a reference axis A—A extending upwards from the main body 202 as shown in FIG. 6. By "inwardly," it is generally meant that the first clamp 240 moves leftward and towards the reference axis A—A such that the lateral distance $D'_L$ between the first clamp 240 and the reference axis A—A is reduced. Similarly, the second clamp 260 is preferably pivotably connected to the main body 202 at or near a pivot position 272. As a result, the second clamp 260 is able to rotate about the pivot 272 such that the upper flange 264 moves inwardly towards the reference axis A—A. By "inwardly," it is generally meant that in the orientation shown in FIG. 5, the second clamp 260 moves rightward and towards the reference axis A—A such that the lateral distance $D'_L$ between the second clamp 260 and the reference axis is reduced.

As a result of this configuration, the electrosurgical device 200 is able to detect a change in dimension of the tissue 280 being treated as thermal energy is introduced to the treatment zone. In particular, in the illustrated embodiment, the electrosurgical device 200 is able to detect the shrinkage or contraction of the tissue 280 being treated as thermal energy is introduced to the treatment zone. Furthermore, the electrosurgical device 200 is able to detect the recovery or expansion of the tissue 280 being treated as the thermal energy (e.g., heat) is removed from the treatment zone. In a preferred embodiment, the electrosurgical device 200 also can include a displacement measurement device 274 for measuring the shrinkage or contraction of the tissue 280 being treated. In particular, the first and second clamps 240, 260 are coupled to a displacement measurement device 274 that measures the angular or rotational displacement of the first and second clamps 240, 260 as thermal energy is introduced to the treatment zone. For example, the first and second clamps 240, 260 can be coupled to a linear potentiometer, optical sensor, spring/force sensor, or other similar sensing device for measuring the angular or rotation displacement of the first and second clamps 240, 260.

The amount of shrinkage or contraction in the tissue 280 can be determined by calculating the displacement of each contact sensors used to engage and detect shrinkage of the tissue 280. In the illustrated embodiment, the amount of shrinkage in the tissue 280 is determined by calculating the angular displacement of the first and second clamps 240, 260. Once the desired shrinkage of the tissue 280 has been achieved, the displacement measurement device 274 can provide a control signal to the electronic control unit 116 (FIG. 1) to reduce or minimize the amount of thermal energy being supplied to treatment zone by regulating the power source 118 (FIG. 1). Alternatively, the first and second clamps 240, 260 can include a mechanical stop (not shown) to prevent shrinkage of the tissue beyond a pre-determined amount or percentage.

As an alternative to using a sensor arrangement to detect a change in dimension in the tissue being treated, a visual indicator can be used to allow the operator or surgeon to visually detect the shrinkage or contraction of the tissue being treated. For example, as shown in FIG. 10, a visual indicator 282 can be used to measure the shrinkage of the tissue 280. In one possible embodiment, the visual indicator 282 can be applied to the surface of the tissue 280. Preferably, the visual indicator 282 is applied to the surface of the tissue 280 between the first and second clamps 240, 260 using a non-toxic ink or other substance capable of being applied to a tissue. In so doing, the operator can visually inspect the indicator 282 as the thermal energy is being introduced into the treatment zone. In particular, as the tissue 280 shrinks due to the thermal energy being supplied to the treatment zone, the visual indicator 282 changes shape. In the illustrated embodiment, the visual indicator 282 prior to the introduction of thermal energy is an elliptical pattern 284. After the tissue 280 shrinks due to the introduction of the thermal energy, the visual indicator 282 shrinks to a circular pattern 284'. Once the visual indicator shrinks to the appropriate pattern, the operator or surgeon can reduce the amount of thermal energy being supplied by the heat delivery modality 210 by regulating the power source 118 (FIG. 1).

The various embodiments described above are provided by way of illustration only and should not be construed to limit the invention. Those skilled in the art will readily recognize the various modifications and changes which may be made to the present invention without strictly following the exemplary embodiments illustrated and described herein, and without departing from the true spirit and scope of the present invention, which is set forth in the following claims.

The claimed invention is:

1. An electrosurgical device comprising:
   (a) a main body having a proximal end and a distal end;
   (b) a heat delivery modality situated and arranged at the distal end of the main body; the heat delivery modality for providing thermal energy to a tissue being treated; and
   (c) a sensor arrangement situated and arranged at the distal end of the main body; the sensor arrangement being configured to engage and detect shrinkage of the tissue being treated; the sensor arrangement comprising first and second clamping members being situated astride the main body;
      (i) the first clamping member including a first end pivotably connected at the main body and a second end opposite the first end; and
      (ii) the second clamping member including a first end pivotably connected at the main body and a second end opposite the first end;
         (A) each of the second ends of the first and second clamping members being constructed and arranged to engage and detect shrinkage of the tissue being treated such that the first and second clamping members rotate inwardly with respect to one another.

2. The electrosurgical device according to claim 1, wherein the heat delivery modality is configured to provide a continuous flow of electrically conductive fluid to the tissue being treated while thermal energy is introduced.

3. The electrosurgical device according to claim 1, wherein the sensor arrangement comprises:
   (a) at least one contact sensor situated and arranged at the distal end of the main body; the at least one contact sensor being constructed and arranged to engage and detect the shrinkage of the tissue being treated.

4. The electrosurgical device according to claim 1, wherein:
   (a) the first clamping member includes a first mechanical stop for limiting the rotation of the first clamping member; and
   (b) the second clamping member includes a second mechanical stop for limiting the rotation of the second clamping member;
      (i) the first and second mechanical stops being configured to limit the rotation of the first and second clamping members when the tissue being treated achieves a pre-determined shrinkage level.

5. The electrosurgical device according to claim 1, wherein:
   (a) the first clamping member includes a first jaw and a second jaw at the second end of the first clamping member; the first and second jaws of the first clamping member being selectively adjustable to grasp the tissue being treated; and
   (b) the second clamping member includes a first jaw and a second jaw at the second end of the second clamping member; the first and second jaws of the second clamping member being selectively adjustable to grasp the tissue being treated.

6. The electrosurgical device according to claim 5, wherein:
   (a) each of the first and second jaws of the first clamping member includes a textured inner surface for resistively contacting the tissue being treated; and
   (b) each of the first and second jaws of the second clamping member includes a textured inner surface for resistively contacting the tissue being treated.

7. The electrosurgical device according to claim 6, wherein:
   (a) each of the first and second jaws of the first clamping member includes a solution delivery channel for delivery of a conductive solution to the tissue being treated; and
   (b) each of the first and second jaws of the second clamping member includes a solution delivery channel for delivery of a conductive solution to the tissue being treated.

8. The electrosurgical device according to claim 1, wherein the heat delivery modality includes:
   (a) a first electrode arrangement operable with the first clamping member; the first electrode arrangement being coupled to a source of radio frequency energy; and
   (b) a second electrode arrangement operable with the second clamping member; the second electrode arrangement being coupled to the source of radio frequency energy.

9. The electrosurgical device according to claim 8, wherein:
   (a) the first electrode arrangement includes at least one wet electrode being coupled to the source of radio frequency energy; and
   (b) the second electrode arrangement includes at least one wet electrode being coupled to the source of radio frequency energy.

10. The electrosurgical device according to claim 1, wherein the heat delivery modality includes a laser configured to provide thermal energy to the tissue being treated.

11. The electrosurgical device according to claim 1 further comprising:
(a) a forceps extending from the distal end of the main body between the first and second clamping members; the forceps including a first arm and a second arm; the first and second arms being selectively adjustable to slidably receive the tissue being treated.

12. The electrosurgical device according to claim 11, wherein the heat delivery modality includes:
(a) a first electrode disposed at the first and of the forceps; the first electrode being coupled to a source of radio frequency energy; and
(b) a second electrode disposed at the second arm of the forceps; the second electrode being coupled to a source of radio frequency energy.

13. The electrosurgical device according to claim 12,
(a) the first electrode includes a wet electrode; and
(b) the second electrode includes a wet electrode.

14. The electrosurgical device according to claim 11, wherein:
(a) the first clamping member includes a first jaw and a second jaw at the second end of the first clamping member; the first and second jaws of the first clamping member being selectively adjustable to grasp the tissue being treated; and
(b) the second clamping member includes a first jaw and a second jaw at the second end of the second clamping member; the first and second jaws of the second clamping member being selectively adjustable to grasp the tissue being treated.

15. The electrosurgical device according to claim 14, wherein:
(a) each of the first and second jaws of the first clamping member includes a textured inner surface for resistively contacting the tissue being treated; and
(b) each of the first and second jaws of the second clamping member includes a textured inner surface for resistively contacting the tissue being treated.

16. The electrosurgical device according to claim 11, wherein:
(a) the first arm of the forceps includes a first solution delivery channel for delivery of a conductive solution to the tissue being treated; and
(b) the second arm of the forceps includes a second solution delivery channel for delivery of a conductive solution to the tissue being treated.

17. The electrosurgical device according to claim 1, the sensor arrangement further being configured to provide input to the heat delivery modality such that the thermal energy being provided by the heat delivery modality is varied according to the shrinkage of the tissue being treated.

18. The electrosurgical device according to claim 1, wherein the thermal energy provided by the heat delivery modality is minimized when the tissue being treated achieves a pre-determined shrinkage level.

19. The electrosurgical device according to claim 1, wherein the sensor arrangement is operably connected to a displacement measurement device for measuring the change in shrinkage of the tissue being treated.

20. The electrosurgical device according to claim 19, wherein the displacement measurement device is a linear potentiometer.

21. The electrosurgical device according to claim 19, wherein the displacement measurement device is an optical sensor.

22. The electrosurgical device according to claim 19, wherein the displacement measurement device is a spring/force sensor.

23. An electrosurgical device comprising:
(a) a main body having a proximal end and a distal end;
(b) a heat delivery modality situated and arranged at the distal end of the main body; the heat delivery modality for providing thermal energy to a tissue being treated; the heat delivery modality being configured to provide a continuous flow of electrically conductive fluid to the tissue being treated while thermal energy is introduced; and
(c) a sensor arrangement situated and arranged at the distal end of the main body; the sensor arrangement being configured to engage and detect shrinkage of the tissue being treated; the sensor arrangement comprising first and second clamping members being situated astride the main body;
(i) the first clamping member including a first end pivotably connected at the main body and a second end opposite the first end; and
(ii) the second clamping member including a first end pivotably connected at the main body and a second end opposite the first end;
(A) each of the second ends of the first and second clamping members being constructed and arranged to engage and detect shrinkage of the tissue being treated such that the first and second clamping members rotate inwardly with respect to one another.

24. The electrosurgical device according to claim 23, wherein:
(a) the first clamping member includes a first jaw and a second jaw at the second end of the first clamping member; the first and second jaws of the first clamping member being selectively adjustable to grasp the tissue being treated; and
(b) the second clamping member includes a first jaw and a second jaw at the second end of the second clamping member; the first and second jaws of the second clamping member being selectively adjustable to grasp the tissue being treated.

25. The electrosurgical device according to claim 24, wherein:
(a) each of the first and second jaws of the first clamping member includes a textured inner surface for resistively contacting the tissue being treated; and
(b) each of the first and second jaws of the second clamping member includes a textured inner surface for resistively contacting the tissue being treated.

26. The electrosurgical device according to claim 24, wherein:
(a) each of the first and second jaws of the first clamping member includes a solution delivery channel for delivery of the conductive solution to the tissue being treated; and
(b) each of the first and second jaws of the second clamping member includes a solution delivery channel for delivery of the conductive solution to the tissue being treated.

27. The electrosurgical device according to claim 23, wherein the heat delivery modality includes:
(a) a first electrode arrangement operable with the first clamping member; the first electrode arrangement being coupled to a source of radio frequency energy; and (b) a second electrode arrangement operable with the second clamping member; the second electrode arrangement being coupled to the source of radio frequency energy.

28. The electrosurgical device according to claim 27, wherein:
   (a) the first electrode arrangement includes at least one wet electrode being coupled to the source of radio frequency energy; and
   (b) the second electrode arrangement includes at least one wet electrode being coupled to the source of radio frequency energy.

29. The electrosurgical device according to claim 23 further comprising:
   (a) a forceps extending from the distal end of the main body between the first and second clamping members; the forceps including a first arm and a second arm; the first and second arms being selectively adjustable to slidably receive the tissue being treated.

30. The electrosurgical device according to claim 29, wherein the heat delivery modality includes:
   (a) a first wet electrode disposed at the first arm of the forceps; the first wet electrode being coupled to a source of radio frequency energy; and
   (b) a second wet electrode disposed at the second arm of the forceps; the second wet electrode being coupled to a source of radio frequency energy.

31. The electrosurgical device according to claim 29, wherein:
   (a) the first clamping member includes a first jaw and a second jaw at the second end of the first clamping member; the first and second jaws of the first clamping member being selectively adjustable to grasp the tissue being treated; and
   (b) the second clamping member includes a first jaw and a second jaw at the second end of the second clamping member; the first and second jaws of the second clamping member being selectively adjustable to grasp the tissue being treated.

32. The electrosurgical device according to claim 31, wherein:
   (a) each of the first and second jaws of the first clamping member includes a textured inner surface for resistively contacting the tissue being treated; and
   (b) each of the first and second jaws of the second clamping member includes a textured inner surface for resistively contacting the tissue being treated.

33. The electrosurgical device according to claim 29, wherein:
   (a) the first arm of the forceps includes a first solution delivery channel for delivery of a conductive solution to the tissue being treated; and
   (b) the second arm of the forceps includes a second solution delivery channel for delivery of a conductive solution to the tissue being treated.

34. The electrosurgical device according to claim 23, the sensor arrangement further being configured to provide input to the heat delivery modality such that the thermal energy being provided by the heat delivery modality is varied according to the shrinkage of the tissue being treated.

35. The electrosurgical device according to claim 23, wherein the thermal energy provided by the heat delivery modality is minimized when the tissue being treated achieves a pre-determined shrinkage level.

36. An electrosurgical device having a proximal end and a distal end, the device comprising an end effector situated at the distal end of the device, the end effector configured to simultaneously provide a fluid and electrical energy to tissue, the electrical energy sufficient to cause a dimension change of the tissue, the end effector comprising:
   (a) at least one electrode configured to provide the electrical energy,
   (b) at least one fluid outlet in fluid communication with a fluid path to provide the fluid, and
   (c) a sensor arrangement having a configuration which moves relative to the dimension change of the tissue to detect the dimension change of the tissue.

37. The electrosurgical device according to claim 36 wherein the dimension change of the tissue is a shrinkage of the tissue.

38. The electrosurgical device according to claim 36 wherein the dimension change of the tissue is an expansion of the tissue.

39. The electrosurgical device according to claim 36, wherein the electrical energy sufficient to change a dimension of the tissue comprises radio frequency electrical energy.

40. The electrosurgical device according to claim 36, wherein the end effector further comprises a first arm and a second arm.

41. The electrosurgical device according to claim 40, wherein:
   (a) the first arm includes a first arm fluid outlet in fluid communication with a first arm fluid path; and
   (b) the second arm includes a second arm fluid outlet in fluid communication with a second arm fluid path.

42. The electrosurgical device according to claim 36, wherein the sensor arrangement comprises at least one contact sensor configured to, at least one of, grasp and embed within the tissue.

43. An electrosurgical device having a proximal end and a distal end, the device comprising an end effector situated at the distal end of the device, the end effector configured to simultaneously provide a fluid and electrical energy to tissue, the electrical energy sufficient to cause a dimension change of the tissue, the end effector comprising:
   (a) at least one electrode configured to provide the electrical energy,
   (b) at least one fluid outlet in fluid communication with a fluid path to provide the fluid, and
   (c) a sensor arrangement configured to detect the dimension change of the tissue and comprising a first clamp and a second clamp separated by a separation distance.

44. The electrosurgical device according to claim 43, wherein the separation distance is adjustable.

45. The electrosurgical device according to claim 36, the sensor arrangement further being configured with the electrode to vary the energy provided by the electrode according to the dimension change of the tissue being treated.

46. The electrosurgical device according to claim 36, wherein the energy provided by the electrode is minimized when the tissue achieves a pre-determined dimension change.

47. An electrosurgical device having a proximal end and a distal end, the device comprising an end effector situated at the distal end of the device, the end effector configured to simultaneously provide a fluid and electrical energy to tissue, the electrical energy sufficient to cause a dimension change of the tissue, the end effector comprising:
   (a) at least one electrode configured to provide the electrical energy,
   (b) at least one fluid outlet in fluid communication with a fluid path to provide the fluid, and (c) a sensor arrangement configured to detect the dimension change of the tissue and operably connected to a displacement measurement device for measuring the dimension change of the tissue.

48. The electrosurgical device according to claim 47, wherein the displacement measurement device comprises a linear potentiometer.

49. The electrosurgical device according to claim 47, wherein the displacement measurement device comprises an optical sensor.

50. The electrosurgical device according to claim 47, wherein the displacement measurement device comprises a spring/force sensor.

51. An electrosurgical device comprising:
    (a) a main body having a proximal end and a distal end;
    (b) a heat delivery modality at the distal end of the main body, the heat delivery modality for providing thermal energy to tissue; and
    (c) a sensor arrangement at the distal end of the main body; the sensor arrangement having a clamp structure to grasp the tissue and detect shrinkage of the tissue.

52. The electrosurgical device according to claim 51 further comprising at least one fluid outlet.

53. An electrosurgical device comprising:
    (a) an end effector region including an arrangement for delivering electrical energy to tissue, the electrical energy sufficient to change a dimension of the tissue; and
    (b) the effector region further including a sensor arrangement having a clamp structure to grasp the tissue and detect the dimension change of the tissue.

54. The electrosurgical device according to claim 53 further comprising at least one fluid outlet.

55. An electrosurgical device comprising:
    (a) an end effector region including an arrangement for delivering electrical energy to tissue, the electrical energy sufficient to change a dimension of the tissue; and
    (b) the effector region further including a sensor arrangement having a clamp structure to grasp the tissue and provide feedback concerning the dimension change of the tissue.

56. The electrosurgical device according to claim 55 further comprising at least one fluid outlet.

57. The electrosurgical device according to claim 56 wherein:
    the at least one fluid outlet comprises at least one fluid outlet hole provided with the end effector region.

58. The electrosurgical device according to claim 55 wherein:
    the clamp structure comprises a first clamp and a second clamp;
    the first clamp comprises a first clamp first jaw member and a first clamp second jaw member; and
    the second clamp comprises a second clamp first jaw member and a second clamp second jaw member.

59. The electrosurgical device according to claim 58 wherein:
    at least one or the first clamp and the second clamp is moveable towards the other clamp.

60. The electrosurgical device according to claim 55 wherein:
    the arrangement for delivering electrical energy to tissue comprises at least a first electrode and a second electrode.

61. The electrosurgical device according to claim 60 wherein:
    the end effector region is configured to provide a fluid simultaneously with the electrical energy;
    the end effector region comprises at least a first fluid outlet hole and a second fluid outlet hole;
    the first fluid outlet hole is positioned to wet the first electrode with the fluid; and
    the second fluid outlet hole is positioned to wet the second electrode with the fluid.

62. The electrosurgical device according to claim 61 wherein:
    the electrical energy comprises radio frequency electrical energy.

63. The electrosurgical device according to claim 54 wherein:
    the at least one fluid outlet comprises at least one fluid outlet hole provided with the end effector region.

64. The electrosurgical device according to claim 53 wherein:
    the clamp structure comprises a first clamp and a second clamp;
    the first clamp comprises a first clamp first jaw member and a first clamp second jaw member; and
    the second clamp comprises a second clamp first jaw member and a second clamp second jaw member.

65. The electrosurgical device according to claim 64 wherein:
    at least one of the first clamp and the second clamp is moveable towards the other clamp.

66. The electrosurgical device according to claim 53 wherein:
    the arrangement for delivering electrical energy to tissue comprises at least a first electrode and a second electrode.

67. The electrosurgical device according to claim 66 wherein:
    the end effector region is configured to provide a fluid simultaneously with the electrical energy;
    the end effector region comprises at least a first fluid outlet hole and a second fluid outlet hole;
    the first fluid outlet hole is positioned to wet the first electrode with the fluid; and
    the second fluid outlet hole is positioned to wet the second electrode with the fluid.

68. The electrosurgical device according to claim 67 wherein:
    the electrical energy comprises radio frequency electrical energy.

* * * * *

UNITED STATES PATENT AND TRADEMARK OFFICE
CERTIFICATE OF CORRECTION

PATENT NO.   : 6,689,131 B2  
DATED        : February 10, 2004  
INVENTOR(S)  : McClurken It is certified that error appears in the above-identified patent and that said Letters Patent is hereby corrected as shown below:

Drawings,
Figure 3, Sheet 3 of 10, please delete "-formerly 142"

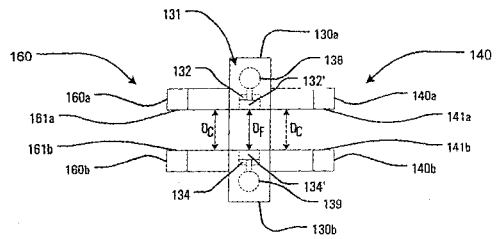

Figure 5, Sheet 5 of 10, please delete "-formerly 142"

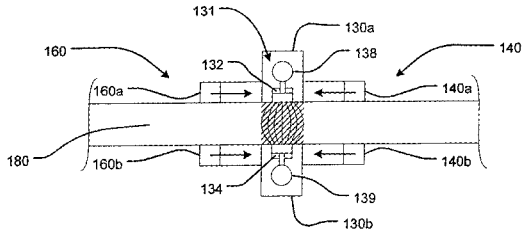

Column 17,
Line 10, "at the first and of" should read -- at the first arm of --

Column 22,
Line 3, "one or the first" should read -- one of the first --

Signed and Sealed this

Fourteenth Day of September, 2004

JON W. DUDAS
*Director of the United States Patent and Trademark Office*